US012566173B2

(12) United States Patent
Shida et al.

(10) Patent No.: US 12,566,173 B2
(45) Date of Patent: Mar. 3, 2026

(54) HEMOLYTIC REAGENT, REAGENT KIT, AND METHOD FOR CLASSIFYING WHITE BLOOD CELLS

(71) Applicant: SYSMEX CORPORATION, Kobe (JP)

(72) Inventors: Yuki Shida, Kobe (JP); Takanori Komaki, Kobe (JP); Daisuke Yokoyama, Kobe (JP); Masaki Abe, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 1023 days.

(21) Appl. No.: 17/672,306

(22) Filed: Feb. 15, 2022

(65) Prior Publication Data

US 2022/0268763 A1 Aug. 25, 2022

(30) Foreign Application Priority Data

Feb. 22, 2021 (JP) ................................ 2021-026612

(51) Int. Cl.

| | |
|---|---|
| ***G01N 33/50*** | (2006.01) |
| ***C07C 43/06*** | (2006.01) |
| ***G01N 1/30*** | (2006.01) |
| ***G01N 21/64*** | (2006.01) |

(52) U.S. Cl.

CPC ......... *G01N 33/5094* (2013.01); *C07C 43/06* (2013.01); *G01N 1/30* (2013.01); *G01N 21/6428* (2013.01); *G01N 2001/302* (2013.01); *G01N 2021/6439* (2013.01)

(58) Field of Classification Search

CPC ...................................................... C07C 43/06

See application file for complete search history.

(56) References Cited

U.S. PATENT DOCUMENTS 4,879,197 A * 11/1989 Kohmura ............... G03G 9/132 430/118.6
6,004,816 A 12/1999 Mizukami et al.
2008/0187990 A1 8/2008 Nagai et al.
2013/0101996 A1 4/2013 Kono et al.
2014/0120530 A1 5/2014 Otsuka et al.
2021/0041341 A1 * 2/2021 Chen .................. G01N 33/5094

FOREIGN PATENT DOCUMENTS

| | | | |
|---|---|---|---|
| EP | 3 654 014 A1 | | 5/2020 |
| JP | 10-319010 A | | 12/1998 |
| JP | 2008-209383 A | | 9/2008 |
| JP | 2012-233754 A | | 11/2012 |
| JP | 5583629 B2 | | 9/2014 |
| JP | 5865009 B2 | | 2/2016 |
| WO | 2012/147578 A1 | | 11/2012 |

OTHER PUBLICATIONS

Extended European Search Report, dated Jul. 8, 2022, issued by the European Patent Office in European Application No. 22155350.6.

Notice of Reasons for Refusal issued Aug. 20, 2024 in Japanese Application No. 2023-094060.

Notice of Reasons for Refusal dated Jan. 17, 2023 issued by the Japanese Patent Office in Japanese Application No. 2021-026612.

* cited by examiner

*Primary Examiner* — Laura L Stockton

(74) *Attorney, Agent, or Firm* — Sughrue Mion, PLLC

(57) ABSTRACT

Disclosed is a hemolytic reagent comprising a nonionic surfactant represented by formula (I) below:

$$R_1—R_2—(CH_2CH_2O)_n—H \quad (I)$$

where $R_1$ represents an alkyl group, an alkenyl group, or an alkynyl group having 8 or more and 25 or less carbon atoms, $R_2$ represents an oxygen atom, (COO) or a group represented by formula (II) below:

(II)

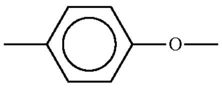

where n is 23 or larger and 25 or smaller, or 30, with n of 23 or larger and 25 or smaller, a concentration of the nonionic surfactant is 1700 ppm or higher and 2300 ppm or lower, and with n of 30, the concentration of the nonionic surfactant is 1900 ppm or higher and 2300 ppm or lower.

16 Claims, 4 Drawing Sheets

HEMOLYTIC REAGENT, REAGENT KIT, AND METHOD FOR CLASSIFYING WHITE BLOOD CELLS

CROSS REFERENCE TO RELATED APPLICATIONS

This application claims priority from prior Japanese Patent Application No. 2021-026612, filed on Feb. 22, 2021, entitled "HEMOLYTIC REAGENT, REAGENT KIT, AND METHOD FOR CLASSIFYING WHITE BLOOD CELLS", the entire contents of which are incorporated herein by reference.

FIELD OF THE INVENTION

The present invention relates to a hemolytic reagent. The present invention also relates to a reagent kit for classifying white blood cells, and a method for classifying white blood cells.

BACKGROUND

Normal white blood cells are classified into five types: lymphocyte, monocyte, neutrophil, eosinophil, and basophil. Information such as classification and count of white blood cells are useful for examining health conditions of subjects. A known reagent for classifying and counting white blood cells is exemplified by a reagent described in U.S. Patent Application Publication No. 2014/0120530. U.S. Patent Application Publication No. 2014/0120530 discloses a hemolytic reagent that contains an aromatic organic acid, and is adjusted to a predetermined pH. According to the description, monocyte and lymphocyte can be accurately classified by using this reagent.

SUMMARY OF THE INVENTION

The scope of the present invention is defined solely by the appended claims, and is not affected to any degree by the statements within this summary.

An object of the present invention is to provide a hemolytic reagent that classifies not only monocyte and lymphocyte, but also neutrophil and eosinophil with higher accuracy, a white blood cell classification reagent kit, and a method for classifying white blood cells.

A hemolytic reagent contains a nonionic surfactant represented by formula (I) below:

$$R_1—R_2—(CH_2CH_2O)_n—H \quad (I)$$

where $R_1$ represents an alkyl group, an alkenyl group, or an alkynyl group having 8 or more and 25 or less carbon atoms, $R_2$ represents an oxygen atom, (COO) or a group represented by formula (II) below:

(II)

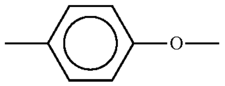

where n in formula (I) is 23 or larger and 25 or smaller, or 30, with n of 23 or larger and 25 or smaller, a concentration of the nonionic surfactant is 1700 ppm or higher and 2300 ppm or lower, and with n of 30, the concentration of the nonionic surfactant is 1900 ppm or higher and 2300 ppm or lower.

The present invention provides a white blood cell classification reagent kit that includes the aforementioned hemolytic reagent, and a staining reagent that fluorescently stains nucleic acid. The present invention also provides a method for classifying white blood cells with use of the aforementioned reagent kit.

According to the present invention, provided are a hemolytic reagent, a reagent kit, and a method for classifying white blood cells, capable of accurately classifying monocyte and lymphocyte, and of accurately classifying neutrophil and eosinophil.

DETAILED DESCRIPTION OF THE PREFERRED EMBODIMENTS

[1. Hemolytic Reagent]

Figure 1A:
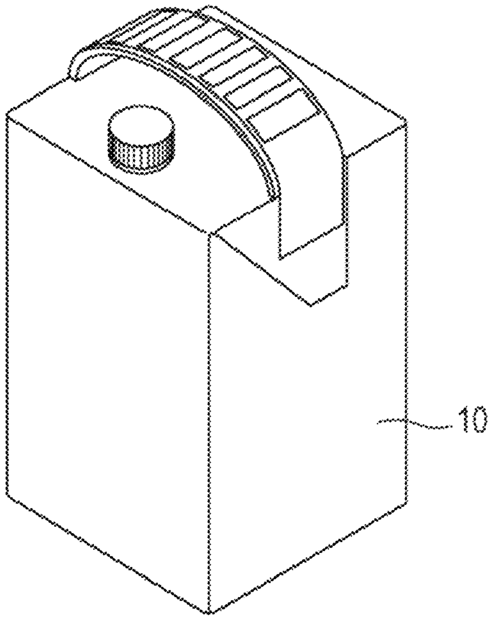
FIG. 1A is a schematic drawing illustrating an exemplary hemolytic reagent of this embodiment.

One embodiment relates to a hemolytic reagent. The hemolytic reagent is a reagent for hemolyzing red blood cells in a sample, and damaging the cell membrane of white blood cells to an extent where a fluorescent dye can permeate therethrough. The hemolytic reagent of the embodiment is suitably used on an automatic hemocytometer capable of classifying the white blood cells contained in a whole blood sample into five populations, which are lymphocyte, monocyte, neutrophil, eosinophil, and basophil, on the basis of flow cytometry. The automatic hemocytometer typically prepares a measurement sample in which red blood cells are hemolyzed, and white blood cells are stained, by mixing a whole blood sample as a blood sample with a hemolytic reagent and a staining reagent that fluorescently stains nucleic acid. The measurement sample is fed to a flow cell, and irradiated with light, whereby optical information is acquired from the white blood cells. The individual white blood cells are classified into the aforementioned five types of populations, on the basis of the thus acquired optical information. This type of automatic hemacytometer is typically disclosed in Japanese Patent Application Laid-Open No. 2008-209383. This type of hemolytic reagent, when mixed by an automatic hemocytometer with a whole blood sample to prepare a measurement sample, can accurately classify lymphocyte and monocyte, as well as more accurately classify neutrophil and eosinophil.

The automatic hemocytometer may have, besides such function of measuring the whole blood sample, a function of measuring a body fluid sample other than the whole blood sample (ascites, joint fluid, pleural effusion, cerebrospinal fluid, bone marrow fluid, bronchoalveolar lavage fluid, peritoneal lavage fluid, and the like). In this case, the hemolytic reagent can also be used for preparing a measurement sample of white blood cells contained in the body fluid sample other than the whole blood sample. The hemolytic reagent can properly discriminate white blood cells contained in the body fluid sample other than the whole blood sample, and can particularly discriminate monocyte from other populations. An automatic blood cell counting apparatus with a function of measuring the body fluid sample other than the whole blood sample is disclosed, for example, in Japanese Patent Application Laid-Open No. 2008-209383.

The hemolytic reagent of the embodiment contains a nonionic surfactant represented by formula (I) below.

$$R_1—R_2—(CH_2CH_2O)_n—H \quad (I)$$

In formula (I), $R_1$ represents an alkyl group, an alkenyl group or an alkynyl group having 8 or more and 25 or less carbon atoms, and $R_2$ represents an oxygen atom, (COO) or a group represented by formula (II) below.

(II)

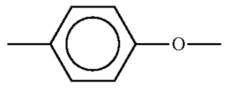

In the hemolytic reagent, a solvent is not particularly limited as long as it can dissolve the nonionic surfactant represented by formula (I). The solvent is exemplified by water, organic solvent, and mixtures thereof. The organic solvent is exemplified by alcohol having 1 to 6 carbon atoms, ethylene glycol, diethylene glycol, polyethylene glycol, and dimethyl sulfoxide (DMSO).

The hemolytic reagent of the embodiment may contain a buffer substance for keeping pH constant. The buffer substance is exemplified by inorganic acid salts, organic acid salts, Good's buffers, and combinations thereof. The inorganic acid salts are exemplified by phosphates, borates, and combinations thereof. The organic acid salts are exemplified by citrate, malate, and combinations thereof. The Good's buffers are exemplified by MES, Bis-Tris, ADA, PIPES, Bis-Tris-propane, ACES, MOPS, MOPSO, BES, TES, HEPES, HEPPS, Tricine, Tris, Bicine, TAPS, and combinations thereof.

In the hemolytic reagent of the embodiment, n in formula (I) is 23 or larger and 25 or smaller. More preferably, n in formula (I) is 23 or 25, and is even more preferably 23. The concentration of the nonionic surfactant represented by formula (I) is 1700 ppm or higher, and preferably 1750 ppm or higher. The concentration of the nonionic surfactant represented by formula (I) is 2300 ppm or lower, and preferably 2200 ppm or lower. In the hemolytic reagent of a further embodiment, the concentration of the nonionic surfactant represented by formula (I) is approximately 1700 ppm or higher, and preferably approximately 1750 ppm or higher. The concentration of the nonionic surfactant represented by formula (I) is approximately 2300 ppm or lower, and preferably approximately 2200 ppm or lower.

In an exemplary hemolytic reagent of the embodiment, n in formula (I) is 23. The concentration of the nonionic surfactant represented by formula (I) is 1700 ppm or higher, and preferably 1750 ppm or higher. The concentration of the nonionic surfactant represented by formula (I) is 2300 ppm or lower, and preferably 2200 ppm or lower. In an example of a hemolytic reagent of a further embodiment, the concentration of the nonionic surfactant represented by formula (I) is approximately 1700 ppm or higher, and preferably approximately 1750 ppm or higher. The concentration of the nonionic surfactant represented by formula (I) is approximately 2300 ppm or lower, and preferably approximately 2200 ppm or lower.

In another exemplary hemolytic reagent of the embodiment, n in formula (I) is 25. The concentration of the nonionic surfactant represented by formula (I) is 1700 ppm or higher, and preferably 1750 ppm or higher. The concentration of the nonionic surfactant represented by formula (I) is 2300 ppm or lower, and preferably 2200 ppm or lower. In still another exemplary hemolytic reagent of a further embodiment, the concentration of the nonionic surfactant represented by formula (I) is approximately 1700 ppm or higher, and preferably approximately 1750 ppm or higher. The concentration of the nonionic surfactant represented by formula (I) is approximately 2300 ppm or lower, and preferably approximately 2200 ppm or lower.

In one aspect of the hemolytic reagent of the embodiment, n in Formula (I) is 30. The concentration of the nonionic surfactant represented by formula (I) is 1900 ppm or higher, more preferably 2000 ppm or higher, and even more preferably 2100 ppm or higher. The concentration of the nonionic surfactant represented by formula (I) is 2300 ppm or lower, and preferably 2200 ppm. In one aspect of the hemolytic reagent of a further embodiment, the concentration of the nonionic surfactant represented by formula (I) is approximately 1900 ppm or higher, preferably approximately 2000 ppm or higher, and more preferably approximately 2100 ppm or higher. The concentration of the nonionic surfactant represented by formula (I) is approximately 2300 ppm or lower, and preferably approximately 2200 ppm or lower.

The nonionic surfactant represented by Formula (I), employable for the hemolytic reagent of the embodiment, is exemplified by polyoxyethylene alkyl ether, polyoxyethylene sterol, polyoxyethylene castor oil, polyoxyethylene sorbitol fatty acid ester, polyoxyethylene alkylamine, polyoxyethylene polyoxypropylene alkyl ether, and combinations thereof. Among them, polyoxyethylene alkyl ether is preferably contained. The polyoxyethylene alkyl ether is preferably at least one selected from the group consisting of polyoxyethylene (23) cetyl ether, polyoxyethylene (25) cetyl ether, and polyoxyethylene (30) cetyl ether. The polyoxyethylene alkyl ether is more preferably polyoxyethylene (23) cetyl ether, polyoxyethylene (25) cetyl ether, or combination thereof, and even more preferably polyoxyethylene (23) cetyl ether. In the hemolytic reagent, the nonionic surfactant may be used singly or in combination of two or more kinds thereof. The hemolytic reagent may further contain a nonionic surfactant other than the nonionic surfactant represented by formula (I).

The hemolytic reagent of the embodiment may further contain a cationic surfactant. The cationic surfactant is exemplified by quaternary ammonium salt type surfactant, pyridinium salt type surfactant, and combinations thereof. The quaternary ammonium salt type surfactant suitably used herein is exemplified by a surfactant represented by formula (III) with a total number of carbon atoms of 9 to 30. The cationic surfactant contained in the hemolytic reagent may be one kind or two or more kinds.

(III)

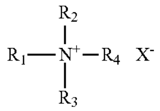

In formula (III), $R_1$ represents an alkyl group or an alkenyl group having 6 to 18 carbon atoms.

$R_2$ and $R_3$ are the same or different from each other, and each represents an alkyl group having 1 to 4 carbon atoms or an alkenyl group. $R_4$ represents an alkyl group having 1 to 4 carbon atoms or an alkenyl group, or a benzyl group, and $X^-$ represents a halogen ion.

In formula (III), $R_1$ preferably represents an alkyl group or an alkenyl group having 6, 8, 10, 12, or 14 carbon atoms, and particularly preferably a linear alkyl group. $R_1$ is more specifically exemplified by octyl group, decyl group, or dodecyl group. Each of $R_2$ and $R_3$ preferably represents a methyl group, an ethyl group, or a propyl group. $R_4$ preferably represents a methyl group, an ethyl group, or a propyl group.

The pyridinium salt type surfactant is typically exemplified by a surfactant represented by Formula (IV).

(IV)

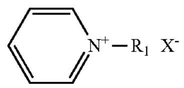

In formula (IV), $R_1$ represents an alkyl group or alkenyl group having 6 to 18 carbon atoms, and $X^-$ represents a halogen atom.

In formula (IV), $R_1$ preferably represents an alkyl group or an alkenyl group having 6, 8, 10, 12, or 14 carbon atoms, and particularly preferably a linear alkyl group. $R_1$ is more specifically exemplified by octyl group, decyl group, or dodecyl group.

In the hemolytic reagent, concentration of the cationic surfactant concentration is suitably selectable depending on the type of surfactant. The concentration of the cationic surfactant is 10 ppm or higher. The concentration is preferably 400 ppm or higher, more preferably 500 ppm or higher, and even more preferably 600 ppm or higher. The concentration of the cationic surfactant is 10000 ppm or lower. The concentration is preferably 1000 ppm or lower, more preferably 800 ppm or lower, and even more preferably 700 ppm or lower.

The hemolytic reagent of the embodiment may further contain an aromatic organic acid. In the present specification, the aromatic organic acid means acid having at least one aromatic ring in the molecule, and salt thereof. The aromatic organic acid is exemplified by aromatic carboxylic acid and aromatic sulfonic acid. The aromatic carboxylic acid is exemplified by phthalic acid, benzoic acid, salicylic acid, hippuric acid, salts thereof, and combinations thereof. The aromatic sulfonic acid is exemplified by p-aminobenzenesulfonic acid, benzenesulfonic acid, salts thereof, and combinations thereof. The aromatic organic acid contained in the hemolytic reagent may be one kind or two or more kinds. Some aromatic organic acid may exhibit a buffering action. In a case where an aromatic organic acid exhibiting a buffering action is used, addition of a buffer solution is optional. Such aromatic organic acid may be combined with the aforementioned buffer solution.

Concentration of the aromatic organic acid, when further contained in the hemolytic reagent, is not specifically limited, which is preferably 20 mM or higher, and more preferably 25 mM or higher, from the viewpoint of performance of classification of monocyte and lymphocyte. Concentration of the aromatic organic acid contained in the hemolytic reagent is preferably 50 mM or lower, and more preferably 45 mM or lower.

In the hemolytic reagent of the embodiment, pH is preferably, but not specifically limited to, 5.5 or higher. The pH is more preferably 5.7 or higher, and even more preferably 5.9 or higher. In the hemolytic reagent, the pH is preferably 7.2 or lower. The pH is more preferably 6.9 or lower, and even more preferably 6.6 or lower. The pH is adjustable with use of any of known bases (such as sodium hydroxide) or acids (such as hydrochloric acid).

In the hemolytic reagent of the embodiment, osmotic pressure is preferably, but not specifically limited to, 150 mOsm/kg or lower, more preferably 130 mOsm/kg or lower, and most preferably 110 mOsm/kg or lower, from the viewpoint of hemolysis efficiency of red blood cells. The osmotic pressure may be adjusted by adding an appropriate osmoregulator. The osmoregulator is exemplified by sugar, amino acid, organic solvent, sodium chloride, and combinations thereof An exemplary reagent kit of this embodiment is illustrated in FIG. 1A. In FIG. 1A, reference numeral 10 denotes a container that contains the hemolytic reagent. The container 10 may further be enclosed typically in a packaging box. The container 10, when enclosed in the package box, may be typically accompanied by a package insert that describes composition of the hemolytic reagent, directions for use, storage and so forth, and a cushion material for cushioning external impact.

[2. White Blood Cell Classification Reagent Kit]

One embodiment relates to a white blood cell classification reagent kit that contains a hemolytic reagent, and a staining reagent that fluorescently stains nucleic acid. The hemolytic reagent contained in the reagent kit is the hemolytic reagent having been described in [1. Hemolytic Reagent].

In the reagent kit, the fluorescent dye that stains nucleic acid is suitably selectable without special limitation, typically depending on wavelength of light irradiated from a light source. The fluorescent dye is exemplified by propidium iodide, ethidium bromide, ethidium-acridine heterodimer, ethidium diazide, ethidium homodimer-1, ethidium homodimer-2, ethidium monoazide, trimethylene bis[[3-[[4-[[(3-methylbenzothiazol-3-ium)-2-yl]methylene]-1,4-dihydroquinolin]-1-yl]propyl]dimethylaminium] tetraiodide (TOTO-1), 4-[(3-methylbenzothiazol-2(3H)-ylidene)methyl]-1-[3-(trimethylaminio)propyl]quinolinium diiodide (TO-PRO-1), N,N,N',N'-tetramethyl-N,N'-bis[3-[4-[3-[(3-methylbenzothiazol-3-ium)-2-yl]-2-propenylidene]-1,4-dihydroquinoline-1-yl]propyl]-1,3-propanediaminium tetraiodide (TOTO-3), or 2-[3-[[1-[3-(trimethylaminio)propyl]-1,4-dihydroquinolin]-4-ylidene]-1-propenyl]-3-methylbenzothiazol-3-ium diiodide (TO-PRO-3), fluorescent dye represented by formula (V) below, and combinations thereof.

(V)

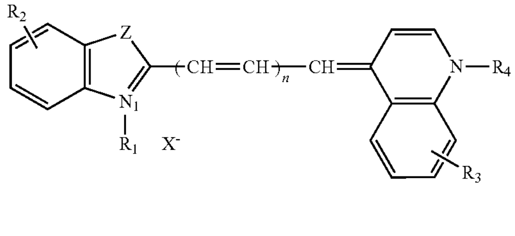

In formula (V), $R_1$ and $R_4$ are same or different from each other, and each represents a hydrogen atom, an alkyl group, an alkyl chain having a hydroxy group, an alkyl chain having an ether group, an alkyl chain having an ester group, or a benzyl group optionally having a substituent. $R_2$ and $R_3$ are the same or different from each other, and each represents a hydrogen atom, a hydroxy group, a halogen atom, an alkyl group, an alkenyl group, an alkynyl group, an alkoxy group, an alkylsulfonyl group or a phenyl group. Z represents a sulfur atom, an oxygen atom, or a carbon atom having a methyl group. n Represents 0, 1, 2, or 3. $X^-$ represents an anion.

In formula (V), the alkyl group may have either linear or branched structure. In a case where either $R_1$ or $R_4$ represents an alkyl group having 6 to 18 carbon atoms, the other preferably represents a hydrogen atom or an alkyl group having less than 6 carbon atoms. Among the alkyl groups having 6 to 18 carbon atoms, preferred is an alkyl group having 6, 8, or 10 carbon atoms.

In formula (V), the substituent on the benzyl group represented by $R_1$ or $R_4$ is exemplified by an alkyl group having 1 to 20 carbon atoms, an alkenyl group having 2 to 20 carbon atoms, or an alkynyl group having 2 to 20 carbon atoms. Among them, preferred is a methyl group or an ethyl group.

In formula (V), the alkenyl group represented by $R_2$ or $R_3$ is exemplified by an alkenyl group having 2 to 20 carbon atoms. The alkoxy group represented by $R_2$ or $R_3$ is exemplified by an alkoxy group having 1 to 20 carbon atoms. Among them, particularly preferred is a methoxy group or an ethoxy group.

In formula (V), the anion $X^-$ is exemplified by a halogen ion such as $F^-$, $Cl^-$, $Br^-$ or $I^-$; $CF_3SO_3^-$ and $BF_4^-$.

In the reagent kit, the fluorescent dye usable herein may be one kind, or two or more kinds. Concentration of the fluorescent dye may be suitably determined depending on the types thereof. The concentration of the fluorescent dye is usually 0.01 pg/μL or higher, preferably 0.1 pg/μL or higher, meanwhile 100 pg/μL or lower, and more preferably 10 pg/μL or lower. In an exemplary case where the fluorescent dye represented by formula (V) is used as the fluorescent dye of one reagent, the concentration of the fluorescent dye in the reagent kit is preferably 0.2 pg/μL or higher, and more preferably 0.3 pg/μL or higher. In an exemplary case where the fluorescent dye represented by formula (V) is used as the fluorescent dye of one reagent, the concentration of the fluorescent dye in the reagent kit is preferably 0.6 pg/μL or lower, and more preferably 0.5 pg/μL or lower.

The reagent kit of the embodiment may employ a commercially available staining reagent for measuring white blood cells, as the staining reagent. Such staining reagent is exemplified by Fluorocell WDF (Sysmex Corporation) and Stromatolyzer 4DS (Sysmex Corporation).

In the reagent kit of the embodiment, the solvent of the reagent contained in the reagent kit is not particularly limited, as long as it can dissolve the nonionic surfactant represented by formula (I) and/or the fluorescent dye. Details of the solvent are the same as those having been described above in [1. Hemolytic Reagent]. The solvent for dissolving therein the fluorescent dye is preferably an organic solvent, from the viewpoint of shelf stability.

In the reagent kit of the embodiment, the solvent of each reagent contained in the reagent kit may contain a buffer substance for keeping the pH constant. Details of the buffer substance are the same as those having been described in [1. Hemolytic Reagent].

Figure 1B:
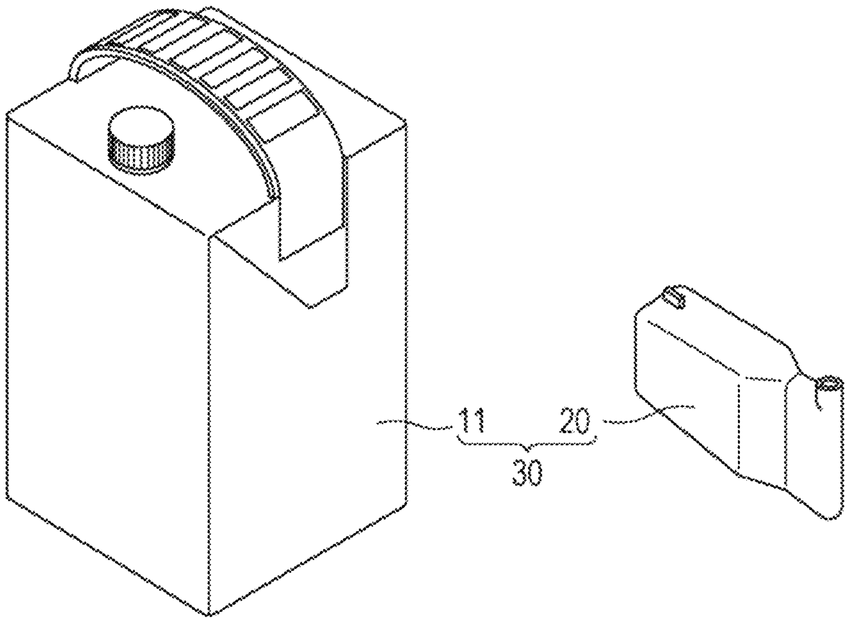
FIG. 1B is a schematic drawing illustrating an exemplary reagent kit of the embodiment.

An exemplary reagent kit of this embodiment is illustrated in FIG. 1B. In FIG. 1B, reference numeral 30 denotes a reagent kit. Reference numeral 11 denotes a first container 11 that contains the hemolytic reagent described in [1. Hemolytic Reagent]. Reference numeral 20 denotes a second container that contains the staining reagent for fluorescently staining nucleic acid. The reagent kit 30 may further be enclosed typically in a packaging box. The reagent kit 30, when enclosed in the package box, may be typically accompanied by a package insert that describes compositions of the individual reagents contained in the reagent kit, directions for use, storage and so forth, and a cushion material for cushioning external impact. The reagent kit 30 may contain other reagent(s), such as buffer solution or a calibrator.

[3. Method for Classifying White Blood Cells]

One embodiment relates to a method for classifying white blood cells. The classification method includes detecting optical information by irradiating a light on a measurement sample prepared by mixing a hemolytic reagent, a staining reagent for fluorescently staining nucleic acid, and a sample that contains white blood cells; and classifying the white blood cells on the basis of the optical information.

In the method of the embodiment, the sample is not specifically limited as long as it is a sample that contains white blood cells, or possibly contains blood cells. The sample that contains white blood cells or possibly contains blood cells is a sample collected from mammal, and preferably from human. The sample is exemplified by whole blood, ascites, joint fluid, pleural effusion, cerebrospinal fluid, bone marrow fluid, bronchoalveolar lavage fluid, peritoneal lavage fluid, urine, and sample collected by apheresis or the like.

For the method of the embodiment, the sample employable here includes a sample diluted with an appropriate aqueous solvent, or a sample to which a known additive is added, as long as the later-described detection process and/or classification process will not be adversely affected. The aqueous solvent is exemplified by water, physiological saline, and buffer solution, without special limitation. The buffer solution preferably demonstrates a buffering action at around neutral pH (6 or higher and 8 or lower, for example). The additive is exemplified by anticoagulant, without special limitation. The anticoagulant is exemplified by K3-EDTA, EDTA, EGTA, TPEN, BAPTA, sodium citrate, warfarin, heparin, danaparoid, fondaparinux, and combinations thereof. Any impurities contained in the sample may be removed by a known method such as centrifugation or filtration.

In the method of the embodiment, a sequential order of mixing the hemolytic reagent, the staining reagent, and the sample is not particularly limited. For example, the hemolytic reagent and the staining reagent may be mixed in advance to prepare a mixed solution, to which the sample may be added. Alternatively, the hemolytic reagent and the sample may be mixed in advance to prepare a mixed solution, to which the staining reagent may be added. Still alternatively, a part of the hemolytic reagent and the sample are mixed in advance to prepare a mixed solution, the thus prepared mixed solution is mixed with the staining reagent, to which the remaining hemolytic reagent may be added lastly.

In the method of the embodiment, mixing ratio of the hemolytic reagent, the staining reagent, and the sample may be appropriately selected, depending on types of the hemolytic reagent, the staining reagent, and the sample. The mixing ratio of the hemolytic reagent, the staining reagent, and the sample is, for example, preferably 1000:(1 or more):(1 or more) on the volume basis. The ratio is more preferably 1000:(10 or more):(10 or more), and even more preferably 1000:(15 or more):(15 or more). In the method of the embodiment, the mixing ratio of the hemolytic reagent, the staining reagent, and the sample is preferably, for example, 1000:(50 or less):(50 or less) on the volume basis. The ratio is more preferably 1000:(30 or less):(30 or less), and even more preferably 1000:(25 or less):(25 or less). The mixing ratio of the staining reagent and the sample may be the same or different.

In the method of the embodiment, irradiation of light on the measurement sample is preferably preceded by incubation. Conditions for the incubation are suitably selectable depending on the sample, without special limitation. For example, incubation temperature is 15° C. or higher, and preferably 30° C. or higher. The incubation temperature is 50° C. or lower, and preferably 45° C. or lower. Incubation time is 5 seconds or longer, preferably 10 seconds or longer, and even more preferably 15 seconds or longer. The incubation time is 120 seconds or shorter, preferably 80 seconds or shorter, and even more preferably 40 seconds or shorter.

In the method of the embodiment, a light is irradiated on the measurement sample, to detect optical information (detection process). The detection process is preferably conducted with use of a flow cytometer. In measurement with use of the flow cytometer, the light is irradiated on the measurement sample contained in the flow cell, to induce signal generation from particles or the like in the measurement sample. The optical information is obtainable by detecting the generated signal. Note that the detection may suitably be preceded by or succeeded by signal processing such as correction, amplification, or conversion, and that also the thus processed signal is encompassed by the optical information.

In the detection process, the light to be irradiated on the measurement sample is not particularly limited, for which a light source having a wavelength suitable for exciting the fluorescent dye is selected. The light source employable here is exemplified by red semiconductor laser, blue semiconductor laser, argon laser, He-Ne laser, and mercury arc lamp. The semiconductor laser is much less expensive than gas laser, and is thus particularly preferred from the viewpoint of cost.

In the detection process, the optical information is not particularly limited as long as it is generally used in flow cytometry. For example, scattered light information, fluorescence information, and so forth may be used. The scattered light is exemplified by forward scattered light (typically scattered light at a light receiving angle of 0° to approximately 20°), and side scattered light (typically scattered light at a light receiving angle of approximately 20° to approximately 90°). The scattered light information and the fluorescence information are exemplified by pulse height, pulse area, pulse width, transmittance, Stokes shift, ratio, temporal change, values correlated thereto, of scattered light and fluorescence. The side scattered light is not particularly limited as long as it represents internal information such as complexity of cellular structure, granule characteristics, nuclear structure, and degree of segmentation.

Figure 2:
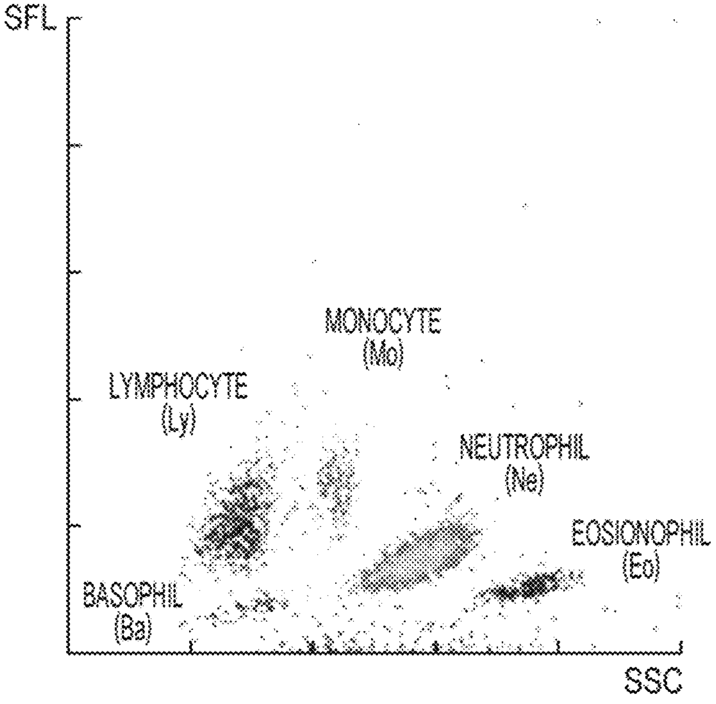
FIG. 2 illustrates an exemplary scattergram of a normal blood sample assayed by using a white blood cell classification reagent kit of the embodiment.

In the method of the embodiment, white blood cells in the measurement sample are classified on the basis of the optical information (classification process). In the classification process, the white blood cells are preferably classified by creating a scattergram having two coordinate axes of side scattered light information and fluorescence information, and analyzing the obtained scattergram with use of appropriate analysis software. For example, when a scattergram is plotted with the side scattered light intensity (SSC) on the X-axis and the fluorescence intensity (SFL) on the Y-axis, as shown in FIG. 2, the white blood cells are classified into five groups of lymphocyte, monocyte, neutrophil, eosinophil, and basophil.

The classification process preferably includes classifying neutrophil population, eosinophil population, monocyte population, and lymphocyte population. It is more preferable to classify a population having the side scattered light intensity higher than the side scattered light intensity of the neutrophil population as the eosinophil population, and to classify a population having the side scattered light intensity lower than the side scattered light intensity of the monocyte population as the lymphocyte population. The side scattered light intensity of each population may be determined, for example, by arithmetically averaging side scattered light intensity values of the individual cells contained in the population, or by calculating a median value of side scattered light intensity values of the individual cells contained in the population.

The method of the embodiment can accurately classify neutrophil and eosinophil. In one example, difference between the side scattered light intensity of the neutrophil population and the side scattered light intensity of the eosinophil population will become larger than that in the prior method, making both populations more clearly classifiable. In another example, the neutrophil population and/or the eosinophil population will have a dispersion in the optical information smaller than that in the prior method, making both populations more clearly classifiable.

The method of the embodiment can accurately classify monocyte and lymphocyte. In one example, difference between the side scattered light intensity of the monocyte population and the side scattered light intensity of the lymphocyte population will become larger than that in the prior method, making both populations more clearly classifiable. In another example, the monocyte population and/or the lymphocyte population will have a dispersion in the optical information smaller than that in the prior method, making both populations more clearly classifiable.

In the method of the embodiment, the dispersion in the side scattered light intensity values may be evaluated, typically by using a statistical index. The statistical index is exemplified by coefficient of variation, standard deviation, and variance.

In the method of the embodiment, the hemolytic reagent contains a nonionic surfactant represented by formula (I) below.

$$R_1—R_2—(CH_2CH_2O)_n—H \quad (I)$$

In formula (I), $R_1$ represents an alkyl group, an alkenyl group or an alkynyl group having 8 or more and 25 or less carbon atoms, and $R_2$ represents an oxygen atom, (COO) or a group represented by formula (II) below.

(II)

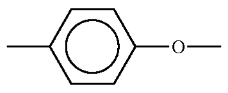

In the method of the embodiment, n in formula (I) is 23 or larger and 25 or smaller. Preferably n in formula (I) is 23 or 25, and more preferably 23. Concentration of the nonionic surfactant represented by formula (I) in the measurement sample is 1650 ppm or higher, and preferably 1700 ppm or higher. The concentration of the nonionic surfactant represented by formula (I) in the measurement sample is 2250 ppm or lower, and preferably 2150 ppm or lower. In the hemolytic reagent of a further embodiment, the concentration of the nonionic surfactant represented by formula (I) in the measurement sample is approximately 1650 ppm or higher, and preferably approximately 1700 ppm or higher. The concentration of the nonionic surfactant represented by formula (I) in the measurement sample is approximately 2250 ppm or lower, and preferably approximately 2150 ppm or lower.

In an exemplary method of the embodiment, n in formula (I) is 23. Concentration of the nonionic surfactant represented by formula (I) in the measurement sample is 1650 ppm or higher, and preferably 1700 ppm or higher. The concentration of the nonionic surfactant represented by formula (I) in the measurement sample is 2250 ppm or lower, and preferably 2150 ppm or lower. In an example of a method of a further embodiment, the concentration of the nonionic surfactant represented by formula (I) in the measurement sample is approximately 1650 ppm or higher, and preferably approximately 1700 ppm or higher. The concentration of the nonionic surfactant represented by formula (I) in the measurement sample is approximately 2250 ppm or lower, and preferably approximately 2150 ppm or lower.

In another exemplary method of the embodiment, n in formula (I) is 25. Concentration of the nonionic surfactant represented by formula (I) in the measurement sample is 1650 ppm or higher, and preferably 1700 ppm or higher. The concentration of the nonionic surfactant represented by formula (I) in the measurement sample is 2250 ppm or lower, and preferably 2150 ppm or lower. In another exemplary method of a further embodiment, the concentration of the nonionic surfactant represented by formula (I) in the measurement sample is approximately 1650 ppm or higher, and preferably approximately 1700 ppm or higher. The concentration of the nonionic surfactant represented by formula (I) in the measurement sample is approximately 2250 ppm or lower, and preferably approximately 2150 ppm or lower.

In one aspect of the method of this embodiment, n in formula (I) is 30. Concentration of the nonionic surfactant represented by formula (I) in the measurement sample is 1850 ppm or higher, preferably 1950 ppm or higher, and more preferably 2050 ppm or higher. The concentration of the nonionic surfactant represented by formula (I) in the measurement sample is 2250 ppm or lower, and preferably 2150 ppm or lower. In one aspect of the method of a further embodiment, the concentration of the nonionic surfactant represented by formula (I) in the measurement sample is approximately 1850 ppm or higher, preferably approximately 1950 ppm or higher, and more preferably approximately 2050 ppm or higher. The concentration of the nonionic surfactant represented by formula (I) in the measurement sample is approximately 2250 ppm or lower, and preferably approximately 2150 ppm or lower.

The method of the embodiment, employed when classifying and counting white blood cells, can improve accuracy of classification not only between monocyte and lymphocyte, but also between neutrophil and eosinophil. The method of one embodiment can also improve the classification accuracy of the monocyte population.

The present invention will be further detailed referring to Examples, to which the present invention is by no means limited.

EXAMPLES

Example 1

Relations among POE chain length of the nonionic surfactant, the accuracy of classification between the neutrophil population and the eosinophil population, and the accuracy of classification between the lymphocyte population and the monocyte population were examined. The accuracy of classification between the neutrophil population and the eosinophil population was evaluated by calculating a difference value (Eo-Ne difference) between the side scattered light intensity of the eosinophil population and the side scattered light intensity of the neutrophil population. The accuracy of classification between the monocyte population and the lymphocyte population was evaluated by calculating a difference value (Mo-Ly difference) between the side scattered light intensity of the lymphocyte population and the side scattered light intensity of the monocyte population.

Dodecyltrimethylammonium chloride (referred to as LTAC, hereinafter) (Tokyo Chemical Industry Co., Ltd.), potassium hydrogen phthalate (Wako Pure Chemical Industries, Ltd.), EDTA-2K (Chubu Chelest Co., Ltd.), and polyoxyethylene (n) cetyl ether (referred to as POE (n) cetyl ether, hereinafter, wherein n represents the degree of polymerization of polyoxyethylene (POE)), which were mixed according to a chemical composition listed in Table 1 below, to prepare each hemolytic reagent. The pH of the hemolytic reagent was adjusted to pH 6.0 with use of NaOH. The staining reagent employed here was Fluorocell WDF (Sysmex Corporation). POE (n) cetyl ether is a nonionic surfactant.

TABLE 1

| Compound | Concentration [ppm] |
|---|---|
| LTAC | 685 |
| POE (n) cetyl ether | 1750 |
| EDTA-2K | 200 |
| Potassium hydrogen phthalate | 8160 |

Fifteen samples of blood collected from healthy human subjects were used as the samples. The flow cytometer employed here was XN-20 (Sysmex Corporation). Each measurement sample was prepared by mixing 1000 μL of the hemolytic reagent, 17 μL of the sample, and 20 μL of the stain solution. The measurement conditions followed the setting of the WDF channel of XN-20 (Sysmex Corporation). Scattergrams were prepared on the basis of the measured values obtained by flow cytometry. Each of the thus prepared scattergrams was analyzed by using proper analytical software to identify the individual populations of white blood cells. The side scattered light intensity and the fluorescence intensity of the individual populations of white blood cells were calculated, on the basis of count of the cells contained in the identified population of white blood cells, the side scattered light intensity, and the fluorescence intensity. The Mo-Ly difference and the Eo-Ne difference were calculated, on the basis of the side scattered light intensity of the individual populations of white blood cells.

Hemolytic reagents were prepared according to the chemical composition listed previously in Table 1, in which the nonionic surfactant was any of POE (20) cetyl ether (Nikko Chemicals Co., Ltd.), POE (25) cetyl ether (Aoki Oil Industrial Co., Ltd.), POE (30) cetyl ether (Nikko Chemicals Co., Ltd.), or POE (40) cetyl ether (Nikko Chemicals Co., Ltd.). The fifteen samples were assayed by flow cytometry, with use of the thus prepared hemolytic reagents. On the basis of measured values, an average value of the Eo-Ne difference among 15 samples, and an average value of the Mo-Ly difference among 15 samples were calculated for each of the hemolytic reagents. Results of Example 1 are summarized in Table 2.

TABLE 2

| | Eo − Ne difference | Mo − Ly difference |
|---|---|---|
| POE (40) cetyl ether | 34.5 | 40.6 |
| POE (30) cetyl ether | 42.1 | 38.7 |
| POE (25) cetyl ether | 50.2 | 36.7 |
| POE (20) cetyl ether | 57.2 | 25.4 |

It was understood from Table 2 that the Eo-Ne difference was likely to become smaller whereas the Mo-Ly difference was likely to become larger, as the degree of polymerization of the POE chain of POE (n) cetyl ether in the hemolytic reagent increased.

Example 2

Relations among the concentration of the nonionic surfactant in the hemolytic reagent, the Eo-Ne difference, and the Mo-Ly difference were examined.

Hemolytic reagents were prepared in the same way as in Example 1, except that POE (23) cetyl ether was used as the nonionic surfactant, that the concentration of POE (23) cetyl ether was varied among 879 ppm, 1318 ppm, 1758 ppm, 1977 ppm, 2197 ppm, 2417 ppm and 2636 ppm, and that the pH was adjusted to 6.1. Hemolytic reagents were also prepared in the same way as in Example 1, except that POE (25) cetyl ether was used as the nonionic surfactant, that the concentration of POE (25) cetyl ether was varied among 879 ppm, 1318 ppm, 1758 ppm, 2197 ppm and 2636 ppm, and that the pH was adjusted to 6.1. Hemolytic reagents were also prepared in the same way as in Example 1 where POE (30) cetyl ether was used as the nonionic surfactant. With use of thus prepared hemolytic reagents, three samples were assayed by flow cytometry. On the basis of measured values, an average value of the Eo-Ne difference among three samples, and an average value of the Mo-Ly difference among three samples were calculated. Results from the cases where POE (23) cetyl ether was used as the nonionic surfactant in the hemolytic reagent are summarized in Table 3, results from the cases where POE (25) cetyl ether was used are summarized in Table 4, and results from the cases where POE (30) cetyl ether was used are summarized in Table 5.

TABLE 3

| POE (23) cetyl ether concentration [ppm] | Eo − Ne difference | Mo − Ly difference |
|---|---|---|
| 879 | 54.0 | 27.3 |
| 1318 | 56 5 | 30.0 |
| 1758 | 60.0 | 38.3 |
| 1977 | 62.5 | 38.7 |
| 2197 | 62.5 | 37.0 |
| 2417 | 62.5 | 32.7 |
| 2636 | 63.0 | 29.0 |

TABLE 4

| POE (25) cetyl ether concentration [ppm] | Eo − Ne difference | Mo − Ly difference |
|---|---|---|
| 879 | 55.0 | 28.0 |
| 1318 | 56.7 | 32.0 |
| 1758 | 60.7 | 39.7 |
| 2197 | 61.7 | 36.0 |
| 2636 | 60.0 | 30.0 |

TABLE 5

| POE (30) cetyl ether concentration [ppm] | Eo − Ne difference | Mo − Ly difference |
|---|---|---|
| 1750 | 45.0 | 40.0 |

It was found from the cases with use of POE (23) cetyl ether or POE (25) cetyl ether, that the Eo-Ne difference was likely to increase as the concentration of the nonionic surfactant increased. It was also found from the cases with use of POE (23) cetyl ether or POE (25) cetyl ether at concentrations from 1758 ppm to 2197 ppm, that classification between the neutrophil and eosinophil, and classification between monocyte and lymphocyte were made clear.

Example 3

Relations among the concentration of POE (23) cetyl ether, the Eo-Ne difference, and the Mo-Ly difference were examined.

Hemolytic reagents were prepared in the same way as in Example 1, except that POE (23) cetyl ether was used as the nonionic surfactant, that the concentration of POE (23) cetyl ether was varied among 1758 ppm, 1933 ppm, 2021 ppm, 2109 ppm, 2197 ppm and 2285 ppm, and that the pH was adjusted to 6.2. Hemolytic reagents were also prepared in the same way as in Example 1 where POE (30) cetyl ether was used as the nonionic surfactant. With use of thus prepared hemolytic reagents, four samples were assayed by flow cytometry. On the basis of measured values, an average value of the Eo-Ne difference among four samples, and an average value of the Mo-Ly difference among four samples were calculated. Results from the cases where POE (23) cetyl ether was used as the nonionic surfactant in the hemolytic reagent are summarized in Table 6, and results from the cases where POE (30) cetyl ether was used are summarized in Table 7.

TABLE 6

| POE (23) cetyl ether concentration [ppm] | Eo − Ne difference | Mo − Ly difference |
|---|---|---|
| 1758 | 54.0 | 42.5 |
| 1933 | 55.8 | 44.0 |
| 2021 | 58.3 | 43.0 |
| 2109 | 57.3 | 42.5 |
| 2197 | 57.8 | 42.0 |
| 2285 | 58.5 | 40.8 |

TABLE 7

| POE (30) cetyl ether concentration [ppm] | Eo − Ne difference | Mo − Ly difference |
|---|---|---|
| 1750 | 39.0 | 42.5 |

It was found from the cases with use of POE (23) cetyl ether, that the Eo-Ne difference was likely to increase as the concentration of the nonionic surfactant increased. It was also found from the cases with use of POE (23) cetyl ether at concentrations of 1758 ppm to 2285 ppm, that classification between the neutrophil and eosinophil, and classification between monocyte and lymphocyte were made clear.

Example 4

The Eo-Ne difference and the Mo-Ly difference were compared among reagent A, reagent B, and reagent C and reagent D.

A hemolytic reagent was prepared in the same way as in Example 1, except that POE (23) cetyl ether was used as the nonionic surfactant, that the concentration of POE (23) cetyl ether was adjusted to 2021 ppm, and that the pH was adjusted to 6.2 (referred to as reagent A, hereinafter). A hemolytic reagent was prepared in the same way as in Example 1, except that POE (25) cetyl ether was used as the nonionic surfactant, that the concentration of POE (25) cetyl ether was adjusted to 1758 ppm, and the pH was adjusted to 6.1 (referred to as reagent B, hereinafter). POE (30) cetyl ether was used as the nonionic surfactant of the hemolytic reagent. A hemolytic reagent was prepared by adjusting concentrations of POE (30) cetyl ether to 2144 ppm, LTAC to 668 ppm, potassium hydrogen phthalate to 5106 ppm, and ADA to 1236 ppm, and by adjusting the pH to 6.5 (referred to as reagent C, hereinafter). A hemolytic reagent was prepared in the same way as in the case of using POE (30) cetyl ether in Example 1 (referred to as reagent D, hereinafter). With use of reagent A, reagent B, reagent C, and reagent D, 132 samples were assayed by flow cytometry in the same way as in Example 1. On the basis of measured values, an average value of the Eo-Ne difference among 132 samples, and an average value of the Mo-Ly difference among 132 samples were calculated.

Figure 3A:
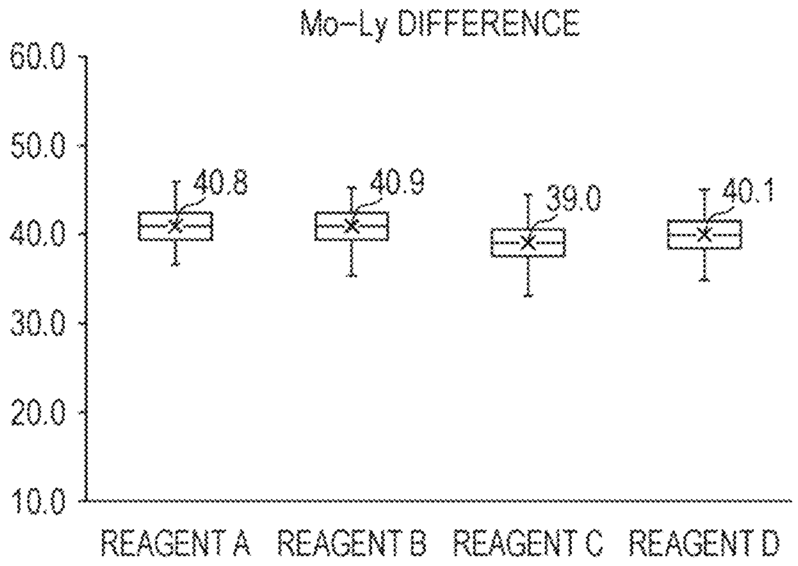
FIG. 3A is a graph illustrating distances between a lymphocyte population and a monocyte population in Example 4.
Figure 3B:
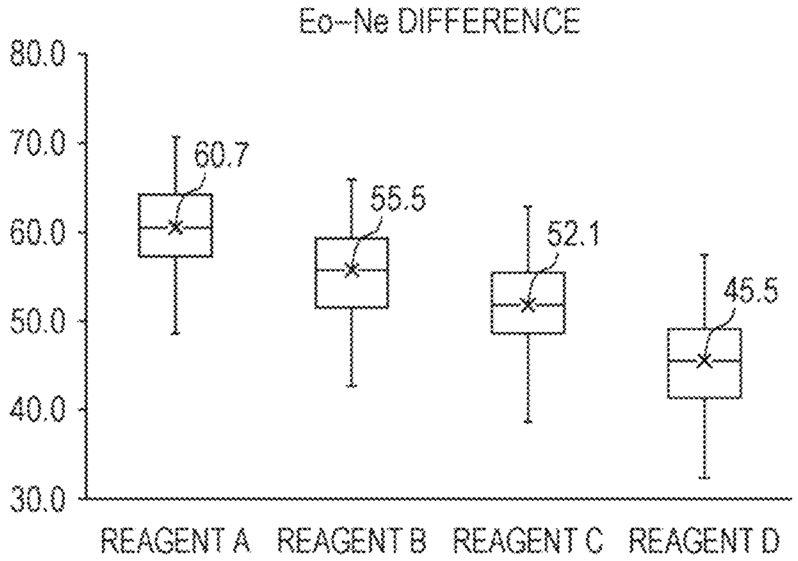
FIG. 3B is a graph illustrating distances between a neutrophil population and an eosinophil population in Example 4.

Results of Example 4 are illustrated in FIGS. 3A and 3B. It was found from FIG. 3B, that the Eo-Ne difference was larger in the case with use of any of reagent A, reagent B, or reagent C, than in the case with use of reagent D. It was also found from FIG. 3A, that the Mo-Ly difference was equivalent in all cases with use of any of reagent A, reagent B, reagent C, or reagent D. It was found that use of reagent A, reagent B, or reagent C enables classification between monocyte and lymphocyte, with an equivalent accuracy compared to that in the case with use of reagent D, and enables classification between neutrophil and eosinophil more accurately than in the case with use of reagent D.

Example 5

Dispersions in the monocyte population were compared between the cases with use of reagent A or reagent D. Dispersions of the monocyte population was evaluated by calculating the coefficient of variation (CV) (referred to as "coefficient of variation of monocyte population", hereinafter), from median (MED) and standard deviation (S.D.) of the fluorescence intensity of white blood cells classified into the monocyte population.

Flow cytometry was conducted in the same way as in Example 1, except that the reagent A or the reagent D prepared in Example 4 was used, and that six samples in total, with breakdowns of four ascites samples (samples 1 to 4), one pleural effusion sample (sample 5), and one joint fluid sample (sample 6), were used. On the basis of the measured values, the coefficient of variation of monocyte population was calculated. Results are summarized in Table 8.

TABLE 8

| | CV(%) | | MED | | S.D. | |
|---|---|---|---|---|---|---|
| Sample | Reagent D | Reagent A | Reagent D | Reagent A | Reagent D | Reagent A |
| 1 | 40.5 | 26.1 | 105 | 109 | 41.7 | 29.5 |
| 2 | 37.7 | 27.6 | 116 | 109 | 42.4 | 31.1 |
| 3 | 43.5 | 27.8 | 133 | 122 | 56.1 | 45.0 |
| 4 | 46.8 | 31.8 | 88.0 | 116 | 38.7 | 31.4 |
| 5 | 43.2 | 35.6 | 91.0 | 117 | 47.2 | 39.1 |
| 6 | 36.4 | 33.3 | 104 | 91.0 | 38.6 | 32.3 |

Figure 4:
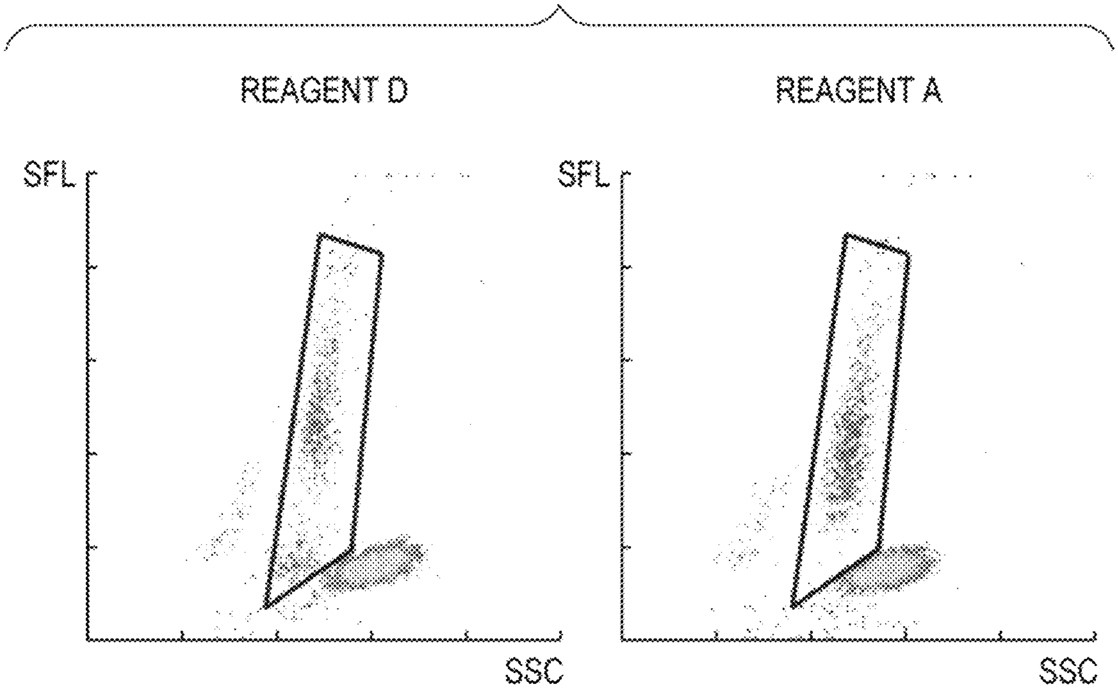
FIG. 4 is a graph illustrating results of scattergram of sample 1 of Example 5.

All of the samples 1 to 6 with use of reagent A were found to give the coefficient of variation of the monocyte population smaller than in the case with use of reagent D. An exemplary scattergram of sample 1 is illustrated in FIG. 4. An area in a frame on the scattergram in FIG. 4 denotes an area where plots of monocyte are expected to appear. In FIG. 4, SSC on the X-axis represents the side scattered light intensity, and SFL on the Y-axis represents the fluorescence intensity. As seen in FIG. 4, also the scattergram proved that the case with use of reagent A gave a dispersion of the fluorescence intensity of the monocyte population, smaller than in the case with use of reagent D.

What is claimed is:

1. A hemolytic reagent comprising a nonionic surfactant represented by formula (I) below:

$$R_1—R_2—(CH_2CH_2O)_n—H \quad (I)$$

where $R_1$ represents an alkyl group, an alkenyl group, or an alkynyl group having 8 or more and 25 or less carbon atoms, $R_2$ represents an oxygen atom, (COO) or a group represented by formula (II) below:

(II)

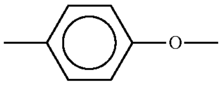

where n is 23 or larger and 25 or smaller, or n is 30, wherein when n is 23 or larger and 25 or smaller, a concentration of the nonionic surfactant is 1700 ppm or higher and 2300 ppm or lower, and when n is 30, the concentration of the nonionic surfactant is 1900 ppm or higher and 2300 ppm or lower.

2. The hemolytic reagent according to claim 1, wherein n in formula (I) is 23 to 25.

3. The hemolytic reagent according to claim 1, wherein the nonionic surfactant is at least one selected from the group consisting of polyoxyethylene (23) cetyl ether, polyoxyethylene (25) cetyl ether, and polyoxyethylene (30) cetyl ether.

4. The hemolytic reagent according to claim 1, further comprising a cationic surfactant.

5. The hemolytic reagent according to claim 4, wherein the cationic surfactant comprises a quaternary ammonium salt type surfactant or a pyridinium salt type surfactant.

6. The hemolytic reagent according to claim 1, further comprising an aromatic organic acid.

7. The hemolytic reagent according to claim 6, wherein the aromatic organic acid is at least one selected from the group consisting of aromatic carboxylic acid, aromatic sulfonic acid, and salts thereof.

8. A white blood cell classification reagent kit comprising the hemolytic reagent according to claim 1, and a staining reagent that fluorescently stains nucleic acid.

9. A method for classifying white blood cells, comprising:
- detecting optical information by irradiating a light on a measurement sample prepared by mixing a hemolytic reagent, a staining reagent for fluorescently staining nucleic acid, and a sample that contains white blood cells; and
- classifying the white blood cells on the basis of the optical information,
- the hemolytic reagent containing a nonionic surfactant represented by formula (I) below:

$$R_1—R_2—(CH_2CH_2O)_n—H \quad \text{Formula (I)}$$

- where $R_1$ represents an alkyl group, an alkenyl group, or an alkynyl group having 8 or more and 25 or less carbon atoms,
- $R_2$ represents an oxygen atom, (COO) or a group represented by formula (II) below:

(II)

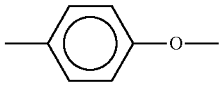

- where n is 23 or larger and 25 or smaller, or 30,
- wherein when n is 23 or larger and 25 or smaller, a concentration of the nonionic surfactant in the measurement sample is 1650 ppm or higher and 2250 ppm or lower, and
- when n is 30, a concentration of the nonionic surfactant in the measurement sample is 1850 ppm or higher and 2250 ppm or lower.

10. The classification method according to claim 9, wherein the optical information is scattered light intensity and fluorescence intensity.

11. The classification method according to claim 9, wherein the optical information is side scattered light intensity.

12. The classification method according to claim 9, wherein the classifying includes classifying a neutrophil population, an eosinophil population, a monocyte population, and a lymphocyte population, among the white blood cells.

13. The classification method according to claim 9, wherein
- the optical information is side scattered light intensity, and
- the classifying comprises:
  - classifying a population, having the side scattered light intensity higher than the side scattered light intensity of the neutrophil population, as the eosinophil population; and
  - classifying a population, having the side scattered light intensity lower than the side scattered light intensity of the monocyte population, as the lymphocyte population.

14. The classification method according to claim 9, wherein n in formula (I) is 23 or larger and 25 or smaller.

15. The classification method according to claim 9, wherein the sample is any of whole blood, ascites, joint fluid, pleural effusion, cerebrospinal fluid, bone marrow fluid, bronchoalveolar lavage fluid, peritoneal lavage fluid, urine, and sample collected by apheresis or the like.

16. The classification method according to claim 9, wherein the detecting the optical information comprises detecting the measurement sample by flow cytometry.

* * * * *